United States Patent
Schoon et al.

(10) Patent No.: US 6,582,419 B1
(45) Date of Patent: Jun. 24, 2003

(54) AORTIC HEART VALVE PROSTHESIS SIZER AND MARKER

(75) Inventors: Thomas G. Schoon, Cedar, MN (US); M. William Mirsch, II, Roseville, MN (US); John F. Otte, St. Anthony, MN (US); Eric S. Buchanan, Wyoming, MN (US); Bob Allan, Maple Grove, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/561,544

(22) Filed: Apr. 28, 2000

Related U.S. Application Data (60) Provisional application No. 60/131,351, filed on Apr. 28, 1999.

(51) Int. Cl.[7] .............................................. A61B 18/18
(52) U.S. Cl. .................................. 606/1; 623/1; 623/2
(58) Field of Search ................................. 606/1; 623/2

(56) References Cited

U.S. PATENT DOCUMENTS

| | | | |
|---|---|---|---|
| 3,828,787 A | * 8/1974 | Anderson et al. ............... 606/1 |
| 3,860,005 A | * 1/1975 | Anderson et al. ............... 606/1 |
| 4,211,241 A | * 7/1980 | Kaster et al. ................ 600/587 |
| 4,679,556 A | * 7/1987 | Lubock et al. ................. 606/1 |
| 5,006,123 A | 4/1991 | Soll et al. .................... 606/166 |
| 5,360,014 A | 11/1994 | Sauter et al. ................ 128/774 |
| 5,443,502 A | * 8/1995 | Caudillo et al. ................ 623/2 |
| 5,476,510 A | * 12/1995 | Eberhardt et al. .............. 623/2 |
| 5,489,296 A | 2/1996 | Love et al. ..................... 623/2 |
| 5,569,237 A | * 10/1996 | Beckenstein .................... 606/1 |
| 5,578,076 A | * 11/1996 | Krueger et al. ................. 623/2 |
| 5,695,503 A | * 12/1997 | Krueger et al. ............. 606/151 |
| 5,697,945 A | 12/1997 | Kritzinger et al. .......... 606/161 |
| 5,814,096 A | 9/1998 | Lam et al. ..................... 623/2 |
| 5,814,101 A | * 9/1998 | Wallner et al. ................. 623/2 |
| 5,906,642 A | * 5/1999 | Caudillo et al. ................ 623/2 |
| 5,980,569 A | * 11/1999 | Scirica .......................... 623/2 |

FOREIGN PATENT DOCUMENTS

WO     WO 97 30659    * 10/1996 ............. A61F/2/24

OTHER PUBLICATIONS

St. Jude Medical Product Literature, "Toronto SPV Valve—Consistent Design For Reproducible Results" (1997).
St. Jude Medical Product Literature, "Implant Considerations For Predictable Results"., pp. 1–10, (1997).
St. Jude Medical® Bioprosthetic Heart Valve, Sizer Set Model B804, Physician's Manual, pp. 2–7; 1997.

* cited by examiner

Primary Examiner—Michael Peffley
Assistant Examiner—Peter J Vrettakos
(74) Attorney, Agent, or Firm—Altera Law Group, LLC (57) ABSTRACT

Improved sizers and markers include a cylindrical section and a handle extending from the cylindrical section. The cylindrical section has a diameter approximately equal to the diameter of an aortic heart valve prosthesis. The cylindrical section can include a marking element configured to mark tissue at fixed positions relative to the cylindrical section. Marking can be performed with a variety of techniques.

40 Claims, 9 Drawing Sheets

AORTIC HEART VALVE PROSTHESIS SIZER AND MARKER

CROSS REFERENCE TO RELATED APPLICATIONS

This application claims priority to U.S. Provisional Patent Application Ser. No. 60/131,351 filed Apr. 28, 1999 to Schoon et al., entitled "Tissue Heart Valve Implantation Tool," incorporated herein by reference.

BACKGROUND OF THE INVENTION

The invention relates to tools that assist with the selection and attachment of aortic heart valve prostheses. In particular, the invention relates to tools to help select a prosthesis with the correct size and markers for marking the aortic tissue to guide placement and attachment of the prosthesis.

Prostheses, i.e., prosthetic devices, are used to repair or replace damaged or diseased organs, tissues and other structures in humans and animals. Prostheses must be generally biocompatible since they are typically implanted for extended periods of time. For example, prostheses can include artificial hearts, artificial heart valves, ligament repair material, vessel repair, surgical patches constructed of mammalian tissue and the like.

Prostheses can be constructed from natural materials such as tissue, synthetic materials or a combination thereof. For example, prostheses formed from purely synthetic materials, such as mechanical heart valve prostheses, can be manufactured, for example, from biocompatible metals, ceramics, carbon materials, such as graphite, polymers, such as polyester, and combinations thereof. Mechanical heart valves can be manufactured with rigid occluders or leaflets that pivot to open and close the valve, or flexible leaf lets that flex to open and close the valve.

Although mechanical heart valves with rigid pivoting occluders have the advantage of proven durability through decades of use, they are associated with blood clotting on or around the prosthetic valve. Blood clotting can lead to acute or subacute closure of the valve or associated blood vessel. For this reason, patients with implanted mechanical heart valves remain on anticoagulants for as long as the valve remains implanted. Anticoagulants impart a 3–5% annual risk of significant bleeding and cannot be taken safely by certain individuals.

Heart valve prostheses can be constructed with flexible tissue leaflets or polymer leaflets. Prosthetic tissue heart valves can be derived from, for example, porcine heart valves or manufactured from other biological material such as bovine pericardium. Biological materials in prosthetic heart valves generally have profile and surface characteristics that provide laminar, nonturbulent blood flow. Therefore, intravascular clotting is less likely to occur than with mechanical heart valves.

However, prosthetic tissue heart valves are limited by a tendency to fail beginning about seven years following implantation. Calcification, i.e., the deposition of calcium salts, especially calcium phosphate (hydroxyapatite), appears to be a major cause of degeneration. Thus, tissue heart valves are generally used for older patients who experience less calcification and require the valve for shorter lengths of time. In addition, various approaches have been developed to reduce the effects of calcification, such that tissue heart valves will have greater durability. As these approaches achieve demonstrated long term effectiveness, tissue heart valves likely will find greater use.

In a heart, blood flow between the respective atria and ventricles and flow from the ventricles are controlled by heart valves. Blood flow from the right ventricle of the heart passes into the pulmonary artery. Blood flow from the left ventricle of the heart passes into the aorta. Blood flow between the left ventricle and aorta passes through the aortic heart valve located near the connection of the aorta with the heart. The natural aortic heart valves has three leaflets that open to allow flow into the aorta and close to prevent back flow into the left ventricle.

Tissue leaflets have sufficient flexibility to open and close. Each of the three leaflets of a natural valve are attached to the cylindrical wall of the aorta along a nonplanar curve. Coronary arteries join the aorta near the valve. A commissure post can block or partially block a coronary artery. This complicates the placement of a stentless aortic prosthesis.

Attachment of a stentless aortic heart valve is complicated since suturing must be performed on both inflow and outflow edges of the valve to secure the valve. Significant pressures are exerted against the valve in use. Due to the pressures, it is desirable to suture the prosthetic valve along the commissure supports to ensure that the valve does not pull away from the aorta. That suturing along the commissure supports is difficult because the valve is within the aorta during the implantation.

SUMMARY OF THE INVENTION

In a first aspect, the invention pertains to a tissue marking device including a generally cylindrical section and a handle attached to the cylindrical section. The generally cylindrical section has a diameter approximately equal to the diameter of an aortic heart valve prosthesis. The cylindrical section includes a marking element configured to mark tissue at fixed positions relative to the cylindrical section.

In another aspect, the invention pertains to a tissue marking device including a generally cylindrical section, a handle attached to the cylindrical section and a marker having a marking tip that interfaces with the cylindrical section. The generally cylindrical section has a diameter approximately equal to the diameter of an aortic heart valve prosthesis. The marker is separately positionable from the cylindrical section.

In a further aspect, the invention pertains to a method for guiding the attachment of an aortic heart valve prosthesis. The method includes marking the aortic tissue to guide the positioning of the prosthesis and the placement of suture.

In addition, the invention pertains to a sizer including a prosthesis template and a handle extending from the prosthesis template. The prosthesis template includes a generally cylindrical section and a plurality of posts along the outflow edge extending upwardly from the generally cylindrical section around the circumference of the cylindrical section. A sizer system can include a plurality of sizing elements with prosthesis templates having different diameters.

DETAILED DESCRIPTION OF THE ILLUSTRATIVE EMBODIMENTS

A sizing and/or marking device can assist with size determination and/or can guide the attachment of aortic heart valve prostheses, particularly stentless tissue-based prostheses. Use of the sizer/marker tool can speed and simplify the valve replacement process. The sizers/markers generally include a section with an outer surface having size and shape corresponding generally to the outer surface of an aortic heart valve prosthesis. This section has a generally cylindrical shape that is roughly planar on one edge of the cylinder and has three posts on the other edge corresponding to the commissure supports of an aortic valve. In alternative embodiments, the sizer/marker is scalloped on one end and has posts extending from the other end of the valve. The sizer marker can also be similarly used in pulmonary valve replacement or other prosthetic heart valve replacement.

A set of the sizers/markers can be used such that a sizer/marker with the correct size for the corresponding prosthesis can be selected by placing the sizer/marker in position within the aorta at the connection with the heart to evaluate the appropriateness of the size. The orientation and clearance of the coronary ostia can also be evaluated with the sizer/marker positioned within the aorta. To assist with manipulation of the tool, a handle can be attached to the section of the sizer/marker that serves as a template for the prosthesis. Also, the device can include structures that can make marks such that the aorta can be marked at positions that indicate how to position the actual prosthesis and/or where to place the sutures. In some embodiments, the sizer/marker includes position indicators such that a separate marking tool can make marks at positions indicated by the properly oriented sizer/marker tool.

Damaged or diseased natural heart valves can be replaced to restore valve function. Heart valve prostheses can be purely mechanical with rigid occluders that pivot on hinges to open and close the valve to provide generally one way flow. Alternatively, heart valve prostheses can be tissue based in which appropriately treated tissue forms flexible leaflets similar in structure to natural tissue leaflets and other parts of the valve. In particular, native heart valves can be harvested and formed into allograft or xenograft prostheses. Xenograft tissue is generally fixed prior to use. In other embodiments, tissue is formed into a structure resembling natural leaflets. Similarly, flexible synthetic materials, especially polymers, can be formed into synthetic leaflets that function similarly to tissue leaflets. The patient can be an animal, especially a mammal, and preferably is a human.

The aortic valve is located between the left ventricle and the aorta. Natural aortic valves have three leaflets, although heart valve prostheses can have a different number of leaflets. The aortic valves are located near the location where the aorta connects to the heart chamber. The placement of an aortic valve prosthesis is complicated by the joining of coronary arteries to the aorta near the valve. Therefore, if the prosthesis is not positioned properly, a commissure support can block or partially block a coronary artery.

Proper positioning of the prosthesis for implantation requires correct placement of the base or inflow edge to ensure proper orientation of the commissure supports. While suturing the prosthesis at the edge of the base is not particularly difficult, care must be taken to place the inflow suture line along a flat plane at the appropriate depth to ensure that the prosthesis clears the coronary ostia, and so that the prosthesis functions properly. If the inflow edge of the prosthesis is also scalloped, similar care must be taken in suturing this type of inflow edge. Suturing the outflow edge of the valve along the scallops and the commissure supports requires additional time to complete the suturing while maintaining the proper position of the prosthesis.

The tools described herein have the general shape of the outer surface of an aortic valve prosthesis. However, the tool does not have to be filled in around the circumference or in the middle as long as the top and bottom edges provide the desired outline of the prosthesis configuration. Therefore, a surgeon can position the sizer/marker in the same way as the actual prosthesis. More accurate size measurements can be performed since the tool has the same exterior shape as the prosthesis. Furthermore, in marking embodiments, marks to aid with suture placement can be made while the surgeon can closely examine the proper placement of the prosthesis without starting the suturing process itself.

To perform the sizing, a plurality of sizing tools are used. By visual observation, the surgeon can make an initial estimate of the proper size. Then, using the estimate as a guide, several sizing tools can be sequentially placed into position in the aorta to obtain an accurate determination of the proper prosthetic size. In preferred embodiments, a set of sizing tools corresponds on a one-to-one basis to the sizes of the available prostheses. The sizing tools are preferably reusable with appropriate sterilization between uses.

The tools also preferably perform a marking function. A properly sized tool in position within the aorta can be used to mark the aorta to guide subsequent attachment of the prosthesis with suture or other fasteners, such as staples. The markings on the aortic wall can indicate the entire surface of the prosthesis, an outline of the prosthesis, the locations of specific suture placement or several reference markings.

In particular, marking can be performed at appropriate locations of the aorta wall with a marking fluid, such as an ink or dye, with a temperature change, such as heat or cold, or with propagated energy, such as electromagnetic radiation, that heats the aortic wall. The marking function can be integral with the sizer in which the sizer/marker emits a marking fluid or transfers energy. Alternatively, the sizer can include position indicators, such as notches, while the actual markings are performed with a separate tool with the guidance of the position indicators. In addition, sutures themselves may be used to indicate valve placement. In that case the position indicating notches could be used to guide suture needle placement for stay sutures.

By using the sizers, the risk of inadvertently using an improper prosthesis size can be reduced. Also, this ability to properly size the prosthesis prior to insertion of an actual prosthesis can provide greater uniformity and speed of implantation to the procedure since the prosthesis placed within the aorta will have the correct size. The sizer/marker tool can be particularly useful in the training of surgeons in the proper implantation of stentless aortic heart valve prostheses. Due to the additional effort required in the implantation of stentless aortic heart valve prostheses, the procedure can be opened up to a greater number of physicians by increasing their confidence in reliably placing the prosthesis in the proper orientation.

Sizer/Marking Tool

The sizer/marker tool generally involves a prosthesis template and a handle extending from the template. The template serves as a sizer to evaluate the proper annular size of the prosthesis. The handle extends from the template to provide for gripping the template when the template is positioned within the aorta. The sizer/marker can be provided with appropriate structure to supply a marking function, as described further below.

Figures 1, 2:
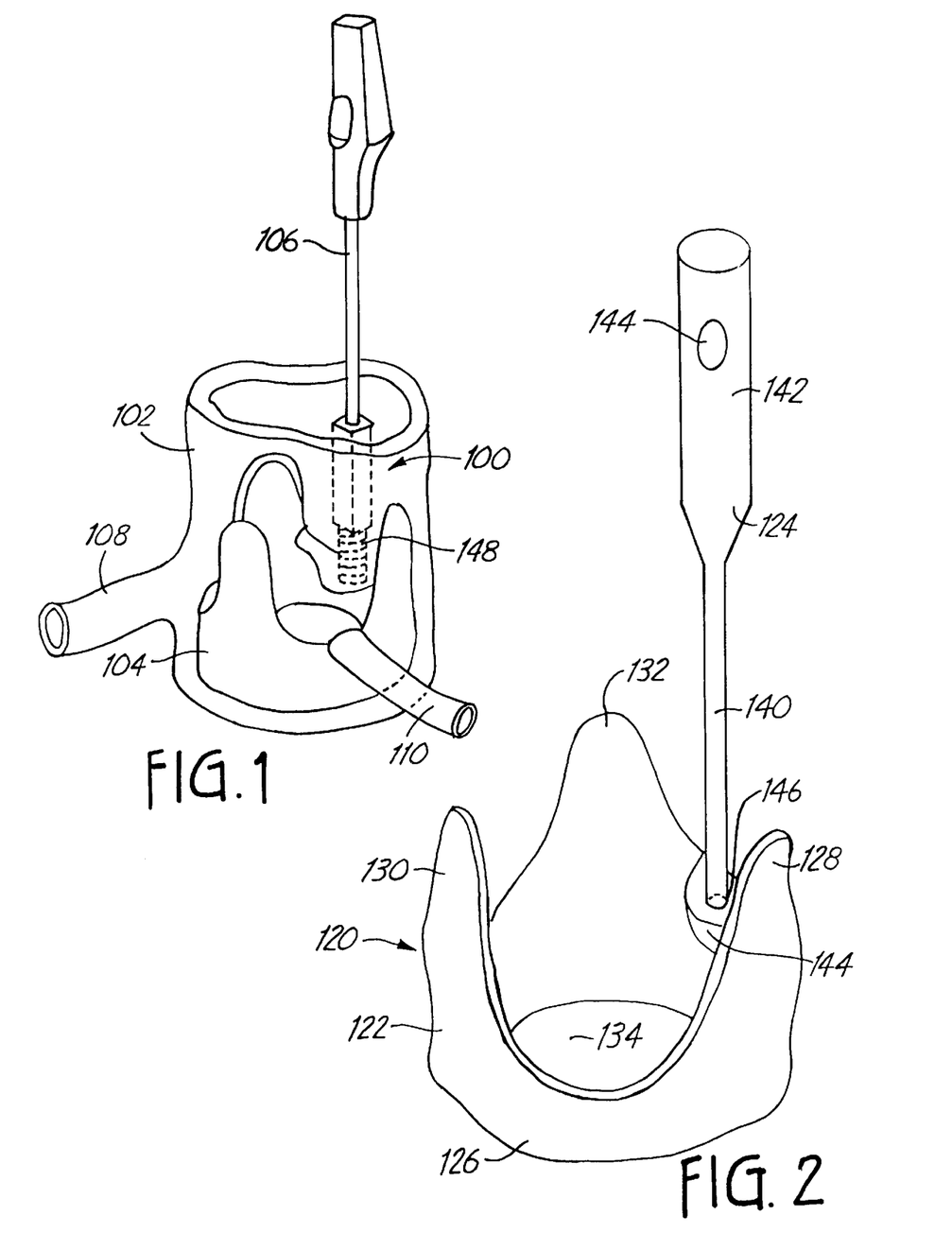
FIG. 1 is a perspective view of a sizer/marker tool positioned within an aorta at its attachment to the heart, in which the aorta is depicted as transparent for illustrative purposes to provide a view of the tool within the aorta.
FIG. 2 is a perspective view of a sizer/marker tool.

Referring to FIG. 1, a sizer/marker 100 is depicted within an aorta 102. Aorta 102 is shown as transparent for illustrative purposes to provide a view of sizer/marker 100 within aorta 102. Sizer/marker 100 includes a prosthesis template 104 and a handle 106. Prosthesis template 104 is positioned within aorta 102 to avoid blockage of openings to coronary arteries 108, 110.

An embodiment of a sizer/marker is shown in FIG. 2. Sizer/marker 120 includes a prosthesis template 122 and a handle 124. Template 122 includes a generally annular base 126 and three posts 128, 130, 132 that simulate commissure supports of a native valve. In preferred embodiments, template 122 includes three posts extending upward from the base corresponding to a prosthetic valve with three leaflets, although different numbers of posts, such as two, can be used for a prosthesis with different numbers of leaflets. Posts 128, 130, 132 are positioned between scalloped sections 134. The preferred structure for the prosthesis template contrasts with the outer structure of a stented aortic tissue valve that has small scalloped flange extending both outwardly and upwardly from a cylindrical section or a sizer that just measures the diameter of the valve annulus. Using the improved sizers, sizing off the ostia yields an inflow edge plane for prosthesis placement, which cannot be obtained just by measuring the annulus.

Handle 124 preferably includes a rigid or malleable shaft 140 and a grip 142. Shaft 140 provides for some flexibility when placing template 122 at the proper location within the aorta. Grip 142 can have any convenient shape for gripping. Grip 142 can include a button 144 or other suitable structure for implementing marking when the sizer/marker is properly positioned within the aorta. If necessary, grip 142 can be connected to an external power supply or the like. Also, grip 142 can include a reservoir of marking fluid or other compositions useful for marking, as described further below.

Handle 124 is attached to template 122 at mount 144. A variety of structures can be used for mount 144. For example, mount 144 can be a ledge or extension located along the inside wall of template 122, as shown in FIG. 2. Alternatively, mount 144 can position extension or shaft 140 at or near the center of template 122, as described below in, for instance, FIGS. 6 and 10. Alternatively, handle 124 may include another extended shaft extending in the opposite direction, in which a second template with a different size is attached to the second extended shaft. In this alternative embodiment, handle 124 has two templates on opposite ends of the handle, such that the surgeon can easily select between the two sizes of templates. Mount 144 can be designed for the permanent attachment of handle 124 to template 122 or for the releasable attachment, such that the handle can be used with other sizer/markers. Releasable attachment can be accomplished with a variety of fasteners 146, such as a screw type attachment 148 (FIG. 1), a bayonet attachment with a compression spring, a snap-fit or other conventional attachment mechanisms. Permanent attachment of the handle can be accomplished, for example, by gluing or welding the shaft 140 of handle 124, or by forming the base around the handle.

Figure 3:
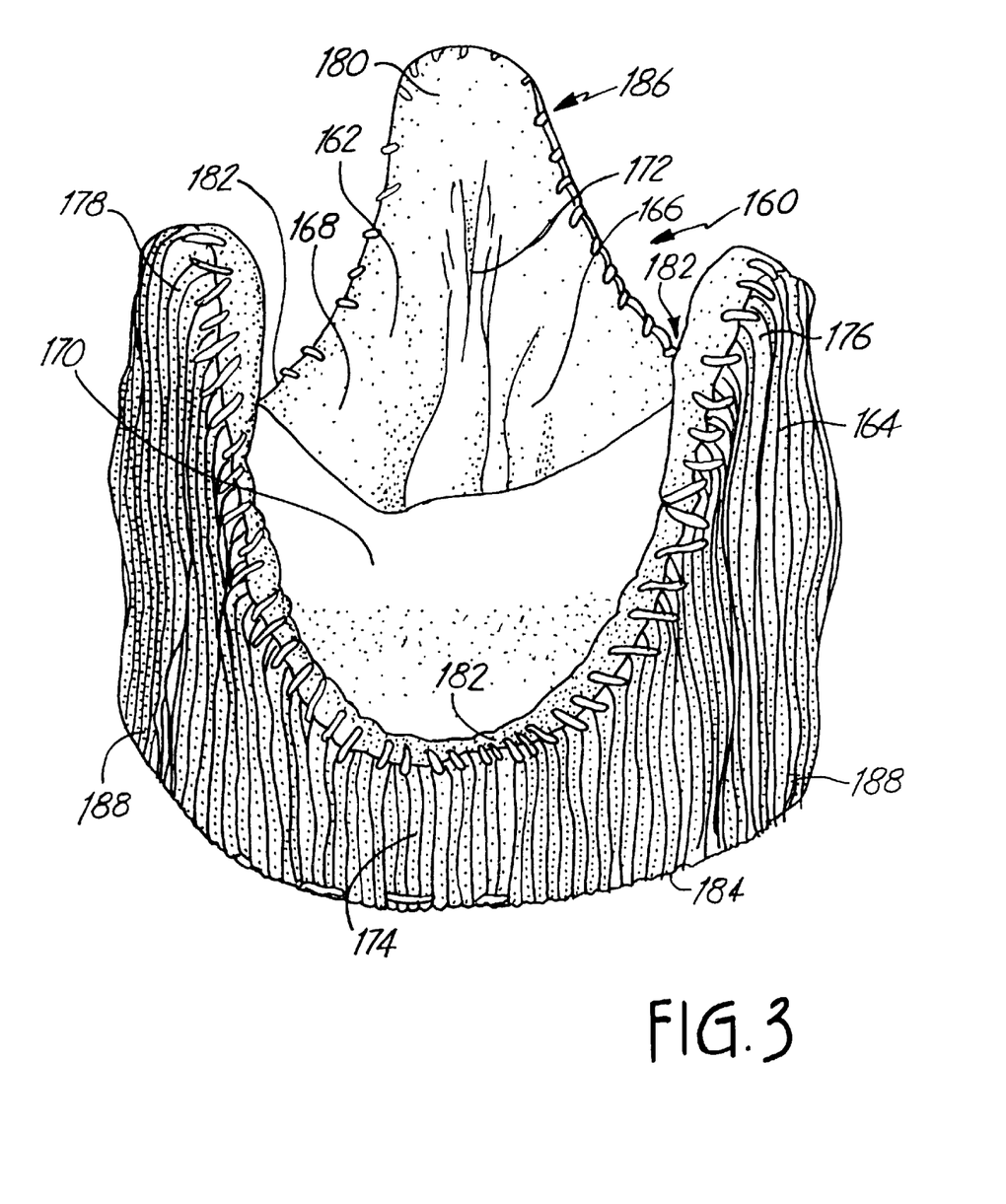
FIG. 3 is a perspective view of an aortic heart valve prosthesis.

The prosthesis template 122 simulates the size and shape from a side view of an aortic heart valve prosthesis, especially a bioprosthetic heart valve. An embodiment of a stentless, tissue heart valve prosthesis is shown in FIG. 3. Heart valve prosthesis 160 includes a harvested tissue valve 162, such as a crosslinked porcine valve. Prosthesis 160 can further include a fabric cover 164. Valve 162 has three leaflets 166, 168, 170 that meet at coaptation surfaces 172. A generally annular base 174 and three commissure supports 176, 178, 180 support the leaflets. When viewed from the side, the spaces between commissure supports 176, 178, 180 form three scallops 182 along the top edge of the prosthesis. Lower edge 184 of prosthesis 160 is the inflow end, and upper edge 186 is the outflow end. In this embodiment, lower edge 184 is generally flat, in contrast with the scalloped upper edge 186 of the prosthesis. Markings 188 can be placed along the lower edge 184 to assist with placement of the valve.

Posts 128, 130, 132 shown in FIG. 2 simulate commissure supports 176, 178, 180 of prosthesis 160 in FIG. 3. Thus, in preferred embodiments, prosthesis template 122 would have a circumference and size and shape of base 126, posts 128, 130, 132, and scallops 134 as a corresponding prosthesis 160. Prosthesis template 122 preferably is formed from a substantially rigid material that will hold its shape when in position. Suitable materials include, for example, biocompatible metal, such as stainless steel or titanium, or polymers, such as polysulfones, polycarbonates, or acetal.

Figure 4:
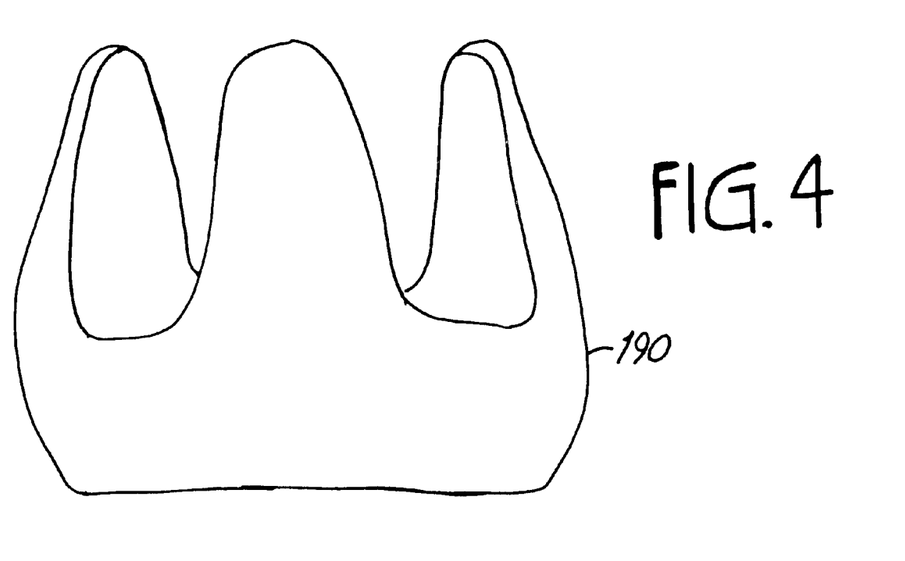
FIG. 4 is a side view of an alternative embodiment of a prosthesis template.
Figure 5:
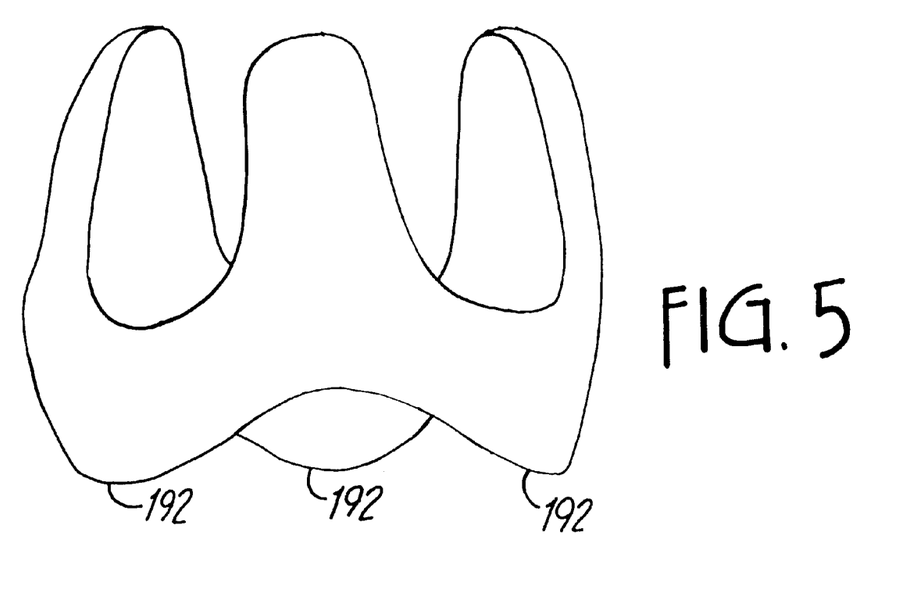
FIG. 5 is a side view of another alternative view of a prosthesis template.

The aortic heart valve prosthesis shown in FIG. 3 has a generally cylindrical profile with a flat lower edge and a scalloped upper edge. In alternative template embodiments, the sizer/marker has a curved, non-cylindrical outer surface 190, as shown in FIG. 4. In addition, the lower, inflow edge can have scallops 192, as shown in FIG. 5. The template of the marker/sizer generally has the overall shape of the corresponding prosthesis, whether or not the profile is cylindrical.

Heart valve prostheses are available in a suitable range of sizes to obtain a proper fit in a patient. Generally, sizer/markers come in corresponding sizes such that once the proper sized tool is identified, the corresponding prosthesis can be selected for implantation. In some embodiments, the prosthesis templates have diameters from about 13 mm to about 39 mm and in other embodiments from about 17 mm to about 31 mm. For example, for the Toronto SPV® aortic valve prostheses available from St. Jude Medical, Inc., the prostheses are commercially available with diameters of 19 mm, 21 mm, 23 mm, 25 mm, 27 mm and 29 mm.

In preferred embodiments, the sizer/marker tool also performs a marking function. The sizer/marker can mark the aorta by contacting the tissue of the aorta with a suitable composition, temperature change or propagating energy field at desired locations to cause a visible mark, as described further below. In alternative embodiments, the sizer/marker includes notches or other suitable position indicators such that a separate marker or suture can be used to mark the tissue by positioning the marker with the assistance of the position indicator. Since the sizer/marker with position indicator provides the desired positioning, the separate marker can interact with the position indicators to provide the mark at the desired location or at other locations desired by the surgeon. The separate marker can similarly mark the aorta with a composition, temperature change or propagating energy. The handle of the sizer/marker or separate marker generally includes a suitable trigger or other actuator to initiate the marking once the marker is at the correct position.

For embodiments based on marking fluids, the prosthesis template component of the sizer/marking tool generally contains pores or openings at desired locations to mark the tissue when the tool is properly positioned. In addition, a reservoir of the fluid can be in the handle or within the prosthesis template itself.

For temperature changes, either cold or hot temperatures can be used to create a color change in the tissue. The temperature change can be created using a fluid with a suitable temperature or by inducing a temperature change at the surface of the marker. In embodiments based on energy propagation, the prosthesis template generally supports transducers that propagate the energy toward the desired locations.

Figure 6:
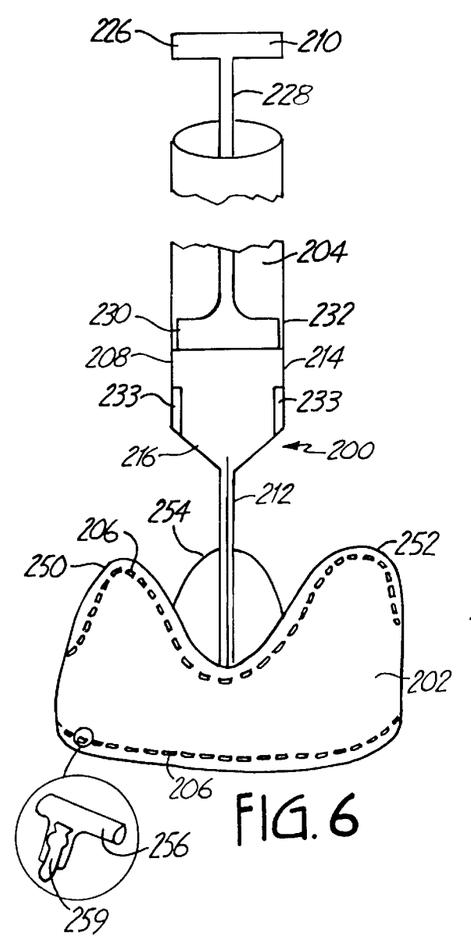
FIG. 6 is a perspective view of a sizer/marker with a handle depicted as transparent for illustrative purposes to show a marking fluid. The insert shows the internal structure surrounding a pore in which the pore has a tip marking material.

An embodiment of a sizer/marker for the delivery of an ink, dye or other marking fluid is shown in FIG. 6. Sizer/marker 200 includes a prosthesis template 202 and a handle 204. Template 202 includes pores 206 in its outer surface. The number and location of the pores are selected to leave desired markings on the aorta. In particular, the pores can outline the prosthesis, for instance, by continuous or broken lines, indicate positions for specific suture placement or provide several reference markings. In the embodiment shown in FIG. 6, a row of pores is located near the inflow edge of the template 202 and a second row of pores is located near the outflow edge along the posts and the scallops. Pores with these locations approximately outline the position of the prosthesis against the aorta.

Handle 204 includes a tubular section 208, a plunger 210 and an extension 212. Tubular section 208 includes a reservoir 214 of marking fluid. Tubular section 208 has a tapered section 216 that connects with extension 212, although section 216 could be other shapes. Plunger 210 includes a grip 226, shaft 228 and plug 230. Grip 226 can be used to move the position of plug 230 to push fluid from reservoir 214. Plug 230 generally has an elastic edge 232 to facilitate movement of plug 230 without losing a liquid tight seal. Ridges or stops 233 can be located within tubular section 208 to stop plunger 210 when sufficient fluid has been dispensed. Alternatively, tubular section 208 can include volume marking to indicate the volume of fluid or a specific amount of fluid required.

Figure 7:
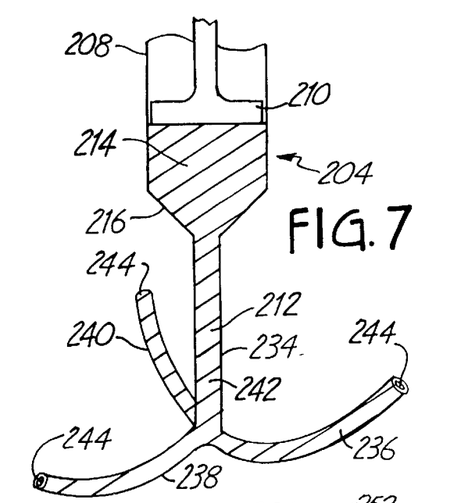
FIG. 7 is a fragmentary view of the handle of the sizer/marker of FIG. 6.

FIG. 7 contains a fragmentary view of the handle 204 with template 202 removed. Extension 212 has a main section 234 and three branches 236, 238, 240, although the number of branches may vary. A channel 242 extends through section 234 and branches 236, 238, 240 such that openings 244 at the ends of branches 236, 238, 240 are in fluid communication with reservoir 214.

Figure 8:
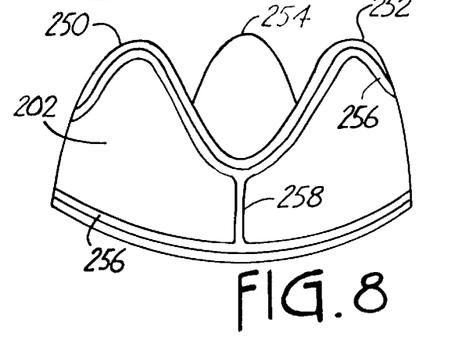
FIG. 8 is a cut-away view of the prosthesis template of the sizer/marker of FIG. 6, in which the surface of the template has been removed to expose internal structure.

Referring to FIGS. 6 and 8, template 202 includes three posts 250, 252, 254. Template 202 with an outer surface removed is shown in FIG. 8. Template 202 includes a series of channels 256 that lead to pores 206 (FIG. 6). As shown in FIG. 8, channels 256 include connecting channels 258 that are not connected to pores but connect other channels with each other.

Openings 244 of branches 236, 238, 240 of FIG. 7 are connected with channels 256 of FIG. 8 in sizer/marker 200. Thus, when grip 226 is depressed, plug 230 pushes liquid from reservoir 214 through extension 212 into channels 256 and out from pores 206. Since template 202 should be positioned snugly against the aorta when marking fluid is released, a small amount of fluid released from the pores should leave localized marks at the location of the pores. Wicking needles, a felt tip 259 (insert of FIG. 6), jets or other similar mechanism could be located in pores 206 to direct and localize the marking fluid.

The marking fluid can be an ink, dye or the like. The marking fluid does not have to be permanent, as long as the mark lasts sufficiently long to complete the implantation process Suitable dyes are biocompatible. Preferred dyes include, for example, methylene blue (Faulding Pharmaceuticals), indigo carmine (Hope Pharmaceuticals), Lymphazurin 1% (U.S. Surgical Corp.), Evan's blue, and commercially available cardiac dyes.

Figure 9:
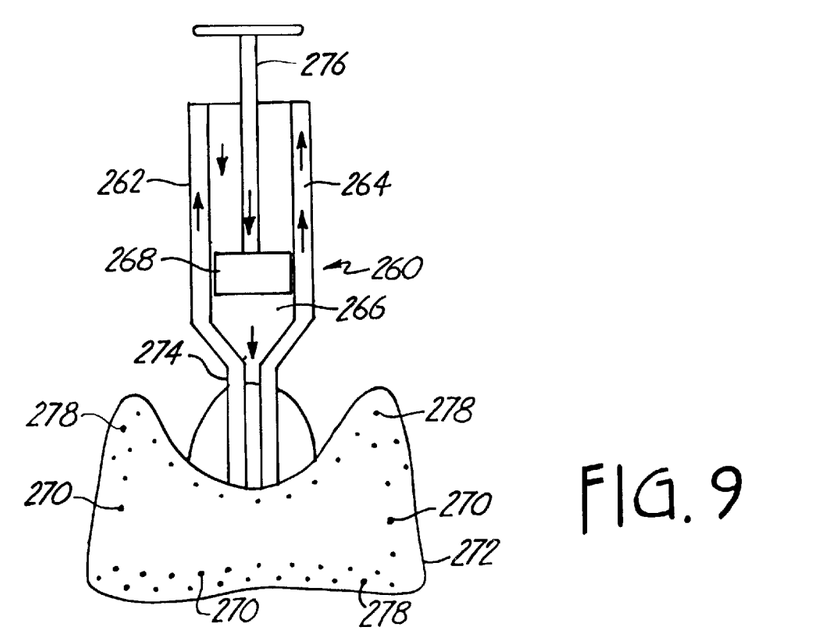
FIG. 9 is a side view of an alternative embodiment of a sizer/marker with a marking fluid, in which the handle is transparent for illustrative purposes, such that internal structure can be observed.

An alternative embodiment of a sizer/marker is shown in FIG. 9. Sizer/marker 260 is similar to the embodiment in FIGS. 6–8, except that sizer/marker 260 includes a tubular section 262 sealed from the ambient environment. Tubular section 262 further includes air channels 264 separated from liquid reservoir 266 by plug 268. Air channels 264 are in fluid connection with a distinct set of holes 270 in the exterior surface of prosthesis template 272 through extender 274. Template 272 includes a set of air channels separate from the fluid channels. When plunger 276 is depressed, the motion of plug 268 forces marking liquid from reservoir 266 through marking holes 278 in template 272 and provides suction at air holes 270 due to reduced pressure in tubular section 262. Suction at air holes 270 holds template 272 in place while the marking fluid is being deposited. The suction available in the surgical room can be used for suction instead of the plunger by connecting air channel 264 with the suction. Other sizer/marker embodiments can also be adapted with suction.

Figure 10:
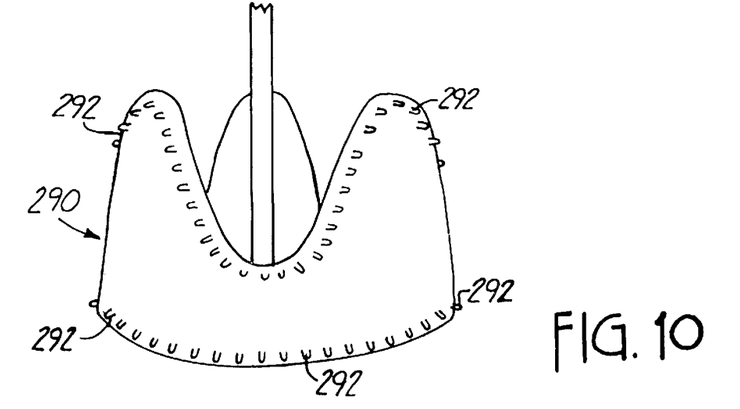
FIG. 10 is a fragmentary side view of a prosthesis template and a portion of the handle, in which the prosthesis template has needles for marking.

Another embodiment of a sizer/marker based on the use of a marking fluid is shown in FIG. 10. Sizer/marker 290 is similar to sizer/marker 200 shown in FIGS. 4–6 except that pores 206 (FIG. 6) are replaced with needles 292 (FIG. 10). Needles 292 are in a sealed placement with pores similar to holes 206 of FIG. 6. Needles 292 include dye or other marking fluid within a small capillary. When the plunger is depressed, movement of the fluid pushes needles 292 outward such that needles 292 extend further from their pores and into the tissue of the aorta. If the plunger is then pulled up, needles 292 withdraw into their pores, and the sizer/marker can be removed. Inserting needles 292 into the aorta wall deposits some of the marking fluid to mark the wall of the aorta below the surface as a tattoo.

As noted above, a low temperature surface can be used to mark the aortic tissue. In particular, cooling fluid can be circulated adjacent the tissue to be marked to freeze the tissue and cause a visible discoloration. If association with the cooling fluid is not maintained for too long of a period of time or at too low of a temperature, the tissue will not be frozen to the point of causing damage to the tissue. Then, the tissue will recover after a brief period of time. The color change of the frozen tissue can last long enough to complete the attachment of the prosthesis. Suitable cooling fluids include, for example, refrigerants, such as, $CO_2$ and freon, and cryogenic fluids, such as, liquid nitrogen, liquid oxygen, liquid helium, and liquid argon.

Figure 11:
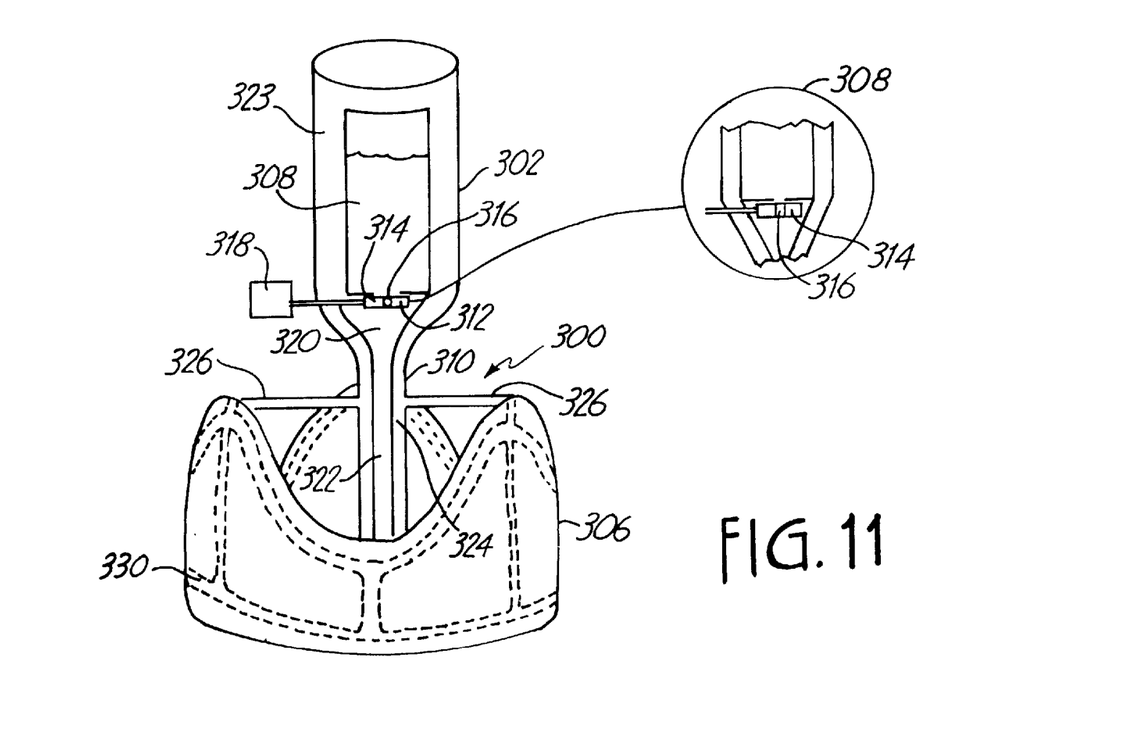
FIG. 11 is a perspective view of a sizer/marker with cooling fluid for marking, in which the handle is transparent for illustrative purposes.

A sizer/marker 300 for marking with a cooling fluid is shown in FIG. 11. Sizer/marker 300 includes a handle 302 and prosthesis template 306. Handle 302 includes a pressure vessel 308 of cooling fluids and an extension 310. Pressure vessel 308 contains a cooling fluid under sufficient pressure to maintain it in the liquid state. Sufficient fluid should be used to obtain a desired temperature drop upon expansion of the fluid. A pressure valve 312 controls the flow of cooling fluid from vessel 308. Valve 312 includes a stopcock 314 with a hole 316. Knob 318 can be used to open and close vessel 308 by rotating stopcock 314. The rotated configuration of stopcock 314 is shown in the cross sectional view in the insert. When open, vessel 308 expands rapidly into channel 320, which extends from handle 302 into extension 310. Extension 310 includes a liquid channel 322 which can be connected to template 306 using arms similar to those shown in FIG. 7. Handle 302 further includes an air channel 323, which provides for venting during flow of cooling fluid. Handle 302 preferably is open to the outside atmosphere.

Template 306 includes liquid channels 330 for cooling fluid within template 306 or on the surface of template 306. Liquid channels 330 are located at positions along template 306 corresponding to desired marking locations for attachment and positioning of the prosthesis. Generally, the surfaces of channels 330 are sufficiently thermal conducting to mark the tissue contacting the surface of the channels. Portions of liquid channels 330 can be insulating to control the resulting markings. Air channel 323 connects to template 306 with vent arms 326. Vent arms 326 include channels that are in fluid communication with liquid channels 330 as well as air channel 323.

After sizer/marker 300 is properly positioned, knob 314 is turned to release cooling fluid. The cooling fluid expands rapidly into extension 310 and then into template 306, thereby cooling liquid channels 330. Vessel 308 can be left open while sizer/marker 300 is removed.

Figure 12:
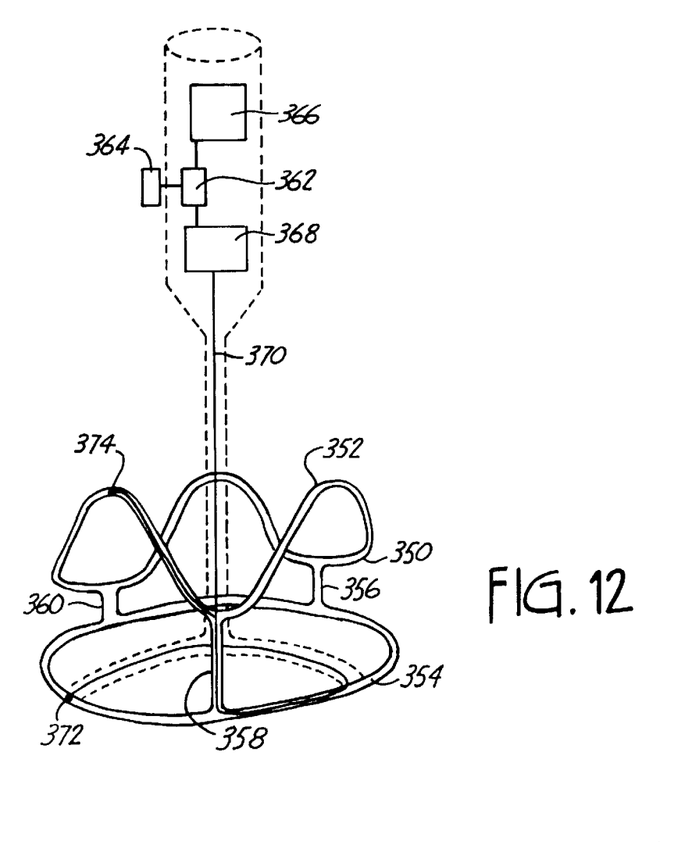
FIG. 12 is a perspective view of a transducer and associated components of a sizer/marker for marking using propagated energy, in which the outline of the handle is shown in phantom lines.

A sizer/marker for marking by heating or energy propagation is shown in FIG. 12. These embodiments result in a tissue that is discolored over the marked regions. In this embodiment, prosthesis template includes a transducer 350. The handle is shown in phantom lines. The template can just include the transducer, or the transducer can be placed over or around an electrically nonconducting support that provides additional structure to the template. If the template just includes the transducer, the transducer preferably provides an outline of the outer shape of the corresponding prosthesis. Transducer 350 includes a scalloped section 352 that generally follows the outflow edge of the prosthesis, a ring section 354 that approximately corresponds to the inflow edge of the prosthesis, and connecting supports 356, 358, 360 between the scalloped section 352 and the ring section 354. The shape of the transducer can be altered to provide a desired set of markings.

The handle generally will include a switch 362, which is controlled by a knob 364. Switch 362 is connected to a power supply 366. Power supply 366 can be, for example, a battery with or without a capacitor, a transformer or a connection to exterior line voltage. An optional oscillator 368 can be connected to switch 362, but oscillator 368 need not be in the handle. Oscillator 368 can be used to generate radio frequency or other frequency alternating currents. Wires 370 connect the components in the handle with transducer 350.

Transducer 350 can be a resistance heater. In these embodiments, scalloped section 352 and ring section 354 are formed from electrically resistive material that heats up when current flows through them. Generally, current is flowed for, at least, several seconds to provide the desired amount of heating. Suitable resistive material includes alloys of chromium, aluminum or both. To obtain appropriate current flow through the desired elements, support 356 can be made from electrically conducting material while supports 358 and 360 are made from electrically insulating material, such as ceramic materials. Wires 370 make electrical contact at connections 372, 374. In these embodiments, direct current or oscillating current can be used.

For radio frequency heating or other electromagnetic radiation based heating, a suitable oscillator 368 is used. The transducer 350 is then a transmitter that propagates electromagnetic energy. Supports 356, 358, 360 can all be electrically insulating. Then, scalloped section 352 and ring section 354 act as counter electrodes for the transmitter.

In one embodiment, the sizer/marker could be connected to a surgical cautery unit, which generates an electrical potential. The surgeon then marks the tissue with an electrical arc discharged from metal conductors on the template of the sizer/marker.

In alternative embodiments, the prosthesis template component of the sizer/marker can include position indicators rather than marking means. Thus, the template provides the capability to mark the aorta at desired locations without actually doing the marking. A separate marker is designed to interface with the position indicators. In other words, the marker tip fits into the position indicators to provide an accurate mark at the locations specified by the position indicators or at other locations desired by the surgeon.

Figure 13:
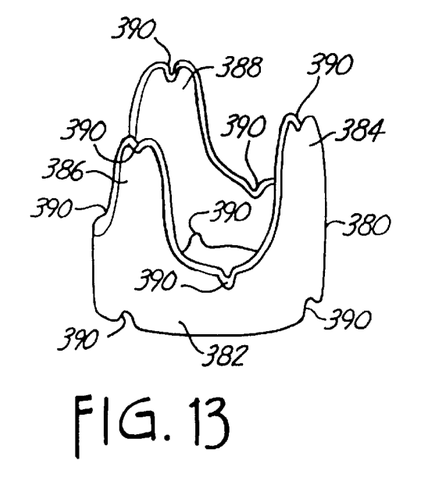
FIG. 13 is a perspective view of a prosthesis template with position indicators for use with a marker or suture needle.

An embodiment of a prosthesis template with position indicators is depicted in FIG. 13. Template 380 has a generally cylindrical base section 382 with three posts 384, 386, 388 extending from base 382. A handle would be appropriately attached to template 380, as discussed above. Position indicators 390 are indentations located, for example, at or near maxima of the posts, at the minima of the scalloped sections in between the posts and at three positions along the bottom or inflow edge of base 382, as shown in FIG. 13.

Figure 14:
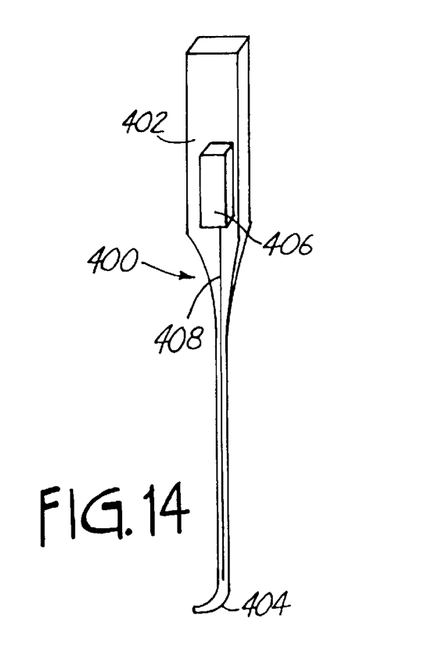
FIG. 14 is a perspective view of a marker for use with the prosthesis template of FIG. 13.

A suitable marker 400 for use with template 380 is depicted in FIG. 14. Marker 400 includes a handle 402 and a tip 404. Handle 402 includes a reservoir 406 that holds marking fluid. Reservoir 406 is connected to a channel 408 that leads to a capillary within tip 404. Tip 404 fits within position indicators 390 shown in FIG. 13, such that carefully placed marks can be made or sutures can be placed with the template in position within the aorta. Alternatively, a hooked implement, such as a blunt ended nerve hook or the like, can be dipped into a marking fluid, such as ink, to perform the marking. In other alternative embodiments, tip 404 is slotted like a nib or has a felt tip like a marker, or some other type of mechanism.

An alternative embodiment of a prosthesis template with position indicators is shown in FIGS. 15–19 for use with aortic xenograft bioprostheses, such as Toronto SPV® heart valve prostheses sold by St. Jude Medical, Inc. Prosthesis template 450 has a slight asymmetry corresponding to the general structure of a porcine valve prosthesis to assist with positioning and marking. Prosthesis template 450 includes a protrusion 452 with a handle connector hole 454 for attaching a handle, for example with a screw attachment, a bayonet attachment or gluing in place.

Figure 15:
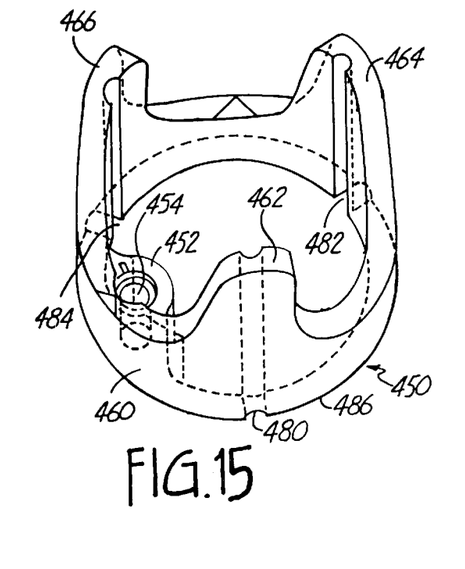
FIG. 15 is a perspective view of a prosthesis template with position indicators.

Template 450 includes a base 460 and three posts 462, 464, 466. The centers of posts 462, 464, 466 may be equally spaced at 120°, but it is preferred to place them asymmetrically at unequal angles that more closely match the anatomical spacing of an aortic porcine heart valve, such as used in the Toronto SPV® valves. Such spacing is approximately 110° between 464 and 466, and 115° between 464 and 462.

Figure 20:
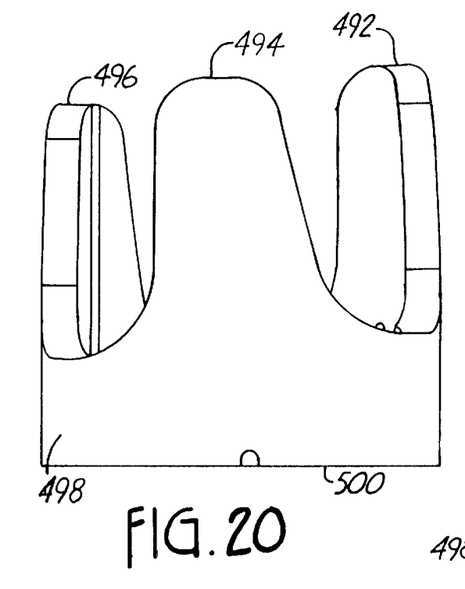
FIG. 20 is a side view of an alternative embodiment of a prosthesis template.
Figure 21:
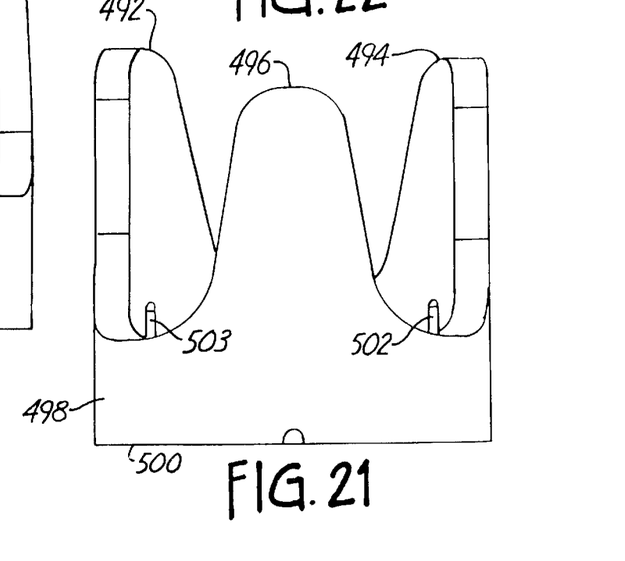
FIG. 21 is another side view of the prosthesis template of FIG. 20.

When the corresponding sizer/marker is properly located, the left coronary sinus and left coronary artery are between posts 464, 466, the right coronary sinus and right coronary artery are between posts 462, 464, and the noncoronary sinus is between posts 462, 466. Alternatively, the left coronary sinus and left coronary artery could be between two of the other posts. The tops of posts 462, 464, 466 may include notches similar to notches 390 in FIG. 13 to guide marking or may be left smooth so that marks or sutures may be placed at any location. The height of each post 462, 464, 466 may be the same, or preferably the heights may be different from each other to approximately match the height of corresponding commissure supports of the bioprosthetic valves, for example the Toronto SPV® valves, such as shown in FIGS. 20 and 21. As shown in FIGS. 20, 21, posts 492, 494, 496 of template 498 have different heights from inflow edge 500.

Figure 16:
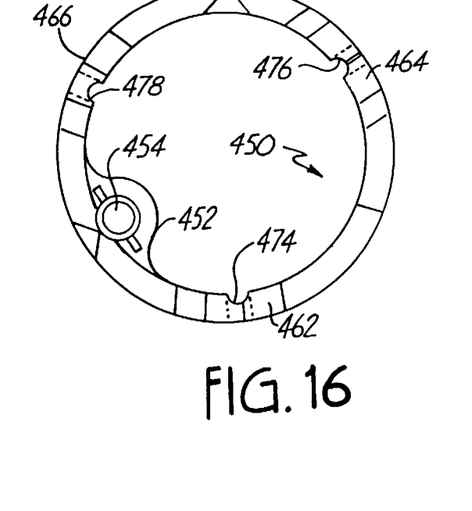
FIG. 16 is a top view of the prosthesis template of FIG. 15.
Figure 17:
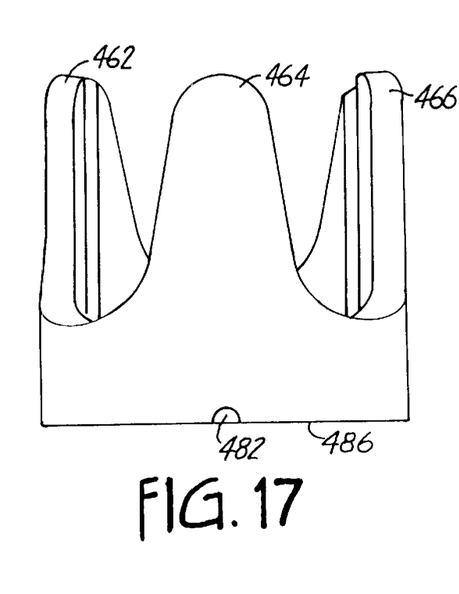
FIG. 17 is a front view of the prosthesis template of FIG. 15, in which a front view corresponds to looking toward extension 464.
Figure 18:
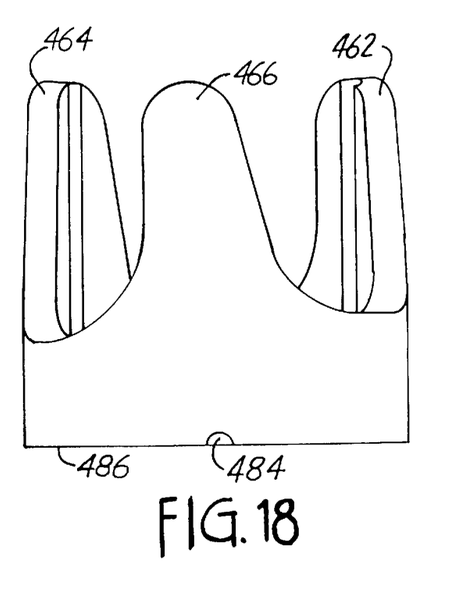
FIG. 18 is a side view of the prosthesis template of FIG. 15.
Figure 19:
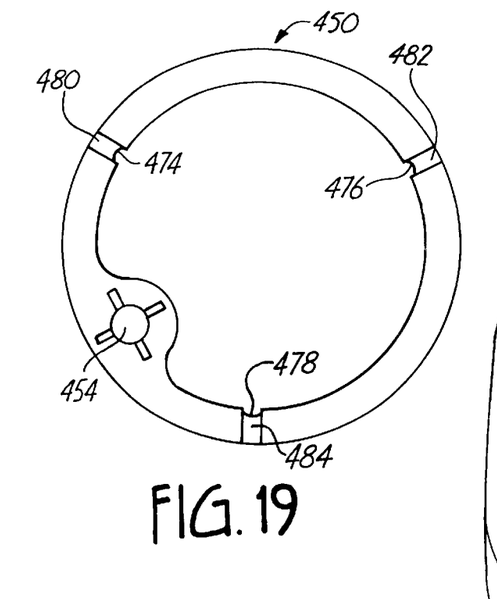
FIG. 19 is a bottom view of the prosthesis template of FIG. 15.
Figure 22:
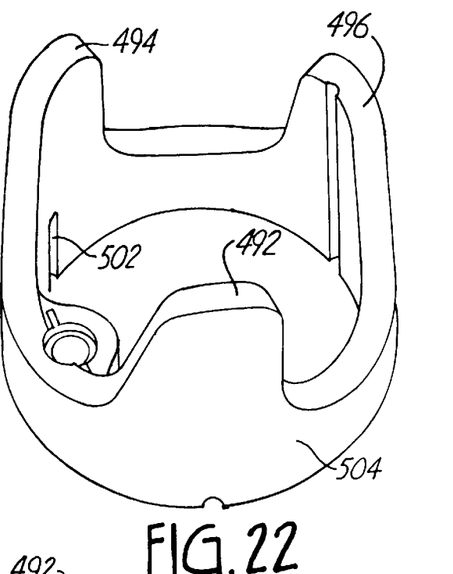
FIG. 22 is a perspective view of the prosthesis template of FIG. 20.

To guide the placement of marks at the bottom or inflow edge of template 450, each post 462, 464, 466 includes guide channels 474, 476, 478, as shown in FIG. 16. Only channel 476 lines up with the center of post 464 to match markings on the Toronto SPV® valve. The angles of the posts 462, 464, 466 are not the same as the angles of notches 480, 482, 484, since posts follow the naturally occurring leaflet coaptation (172 in FIG. 3), and the notches align to markings 188 in FIG. 3. Channels 474, 476, 478 may extend completely from approximately the top to the bottom of the posts of template 450, as shown in FIGS. 15, 17 and 18, or channels 502, 503 can extend partially from top to the bottom of the posts of template 504, as shown in FIGS. 21 and 22. Channels 474, 476, 478 are spaced apart approximately 120 degrees relative to a center line. Channels 474, 476, 478 lead to three notches 480, 482, 484 along inflow edge 486 of template 450, as shown in FIGS. 15 and 17–19.

Thus, using the tops, optionally including notches 390, of posts 462, 464, 466 and notches 480, 482, 484, six marks can be made with, for instance, marker 404 or sutures. Three of the marks correspond to the tops of the commissure supports of the prosthesis, and three of the marks correspond to three suture guide markings 188 (FIG. 3) found along the inflow edge of the Toronto SPV® valves spaced at approximately 120 degrees relative to each other. These six visual reference points can be used to position the prosthesis.

Figure 23:
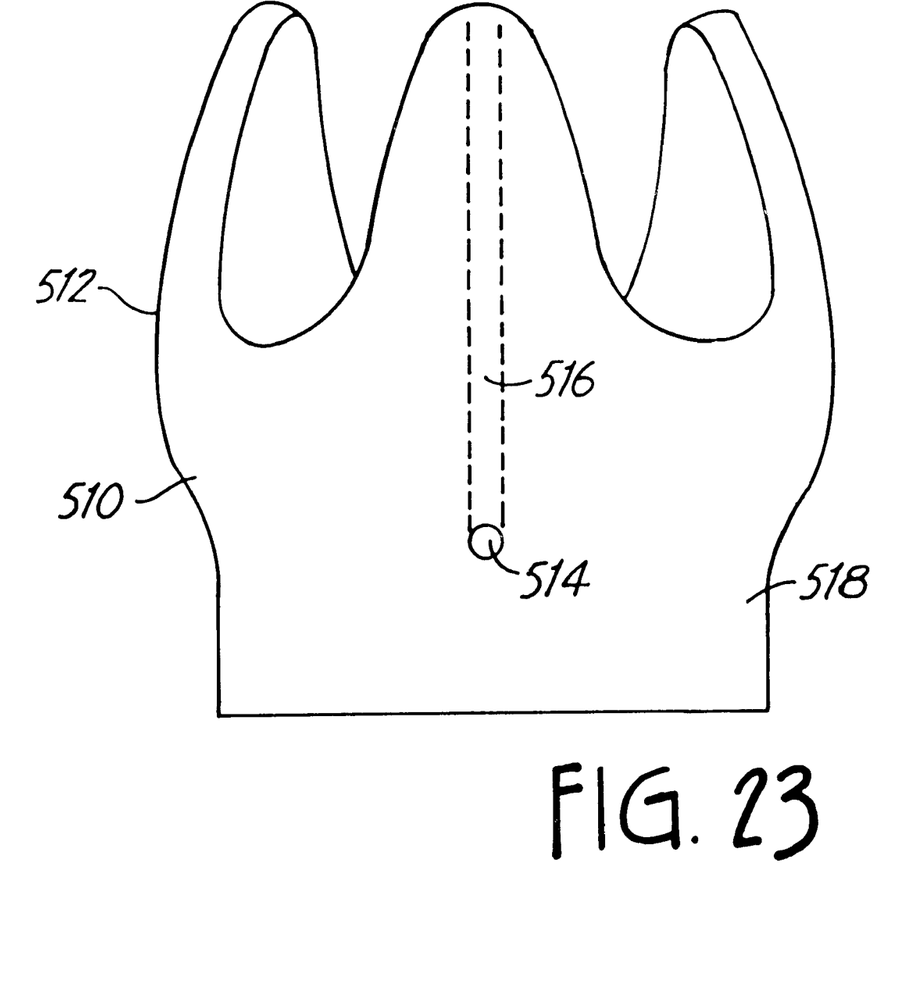
FIG. 23 is a side view of a further embodiment of a prosthesis template.

An alternative embodiment of a template with position indicators is shown in FIG. 23. Template 510 has curved outer surfaces 512 that match the aortic sinuses of the prosthetic valve. One marking hole 514 through the side of the template is shown in FIG. 23. A channel 516 leading to marking hole 514 is shown in phantom lines. In preferred embodiments, two additional marking holes and channels would be located at approximately 120° from the marking hole shown. Template 510 includes a subannular cylindrical sizing section 518 extending below the marking holes for sizing the heart valve annulus.

Use of Sizer/Marking Tool

The sizer/markers described herein can be used to facilitate the selection and implantation of an aortic heart valve prosthesis. Sizing and marking are performed following the removal of the damaged or diseased natural heart valve prior to implantation of the replacement heart valve prosthesis. The use of the sizer/marker can improve the consistency of the replacement procedure, decrease the complexity of the attachment of the prosthesis and reduce the implantation time.

As with any open heart procedure, the process is initiated by placing the patient on appropriate life support and by opening the chest cavity to make the heart accessible. Then, a transverse aortotomy is performed to make the natural valve accessible through the aorta. The preferred location for opening the aorta may depend on precise structure of the prosthesis. For a Toronto SPV® prosthesis, the aorta is cut about 1 cm above the sinotubular junction. The damaged or diseased natural valve leaflets are removed, preferably along with the calcium and calcific debris.

The aortic valve prosthesis generally is placed between the aortic annulus, a slight narrowing where the aorta joins the heart, and the sinotubular junction, a slight narrowing of the aorta just down stream from the coronary arteries. However, the prosthesis can extend beyond the aortic annulus and/or the sinotubular junction. If desired, an initial measurement can be made of the diameter of the aortic annulus and/or the sinotubular junction. With or without making initial measurements, a sizer is selected and inserted, to the extent possible, into the position such that the prosthesis template of the sizer is in the correct position corresponding to the prosthesis. The surgeon can then evaluate the appropriateness of the size of the sizer tool. At the discretion of the surgeon, the surgeon can similarly place one or more additional sizers into position to evaluate aortic size. After positioning one or more sizers within the aorta, the surgeon selects a sizer that has a desired size relative to the patient's aorta. Then, a corresponding prosthesis with the same size can be obtained for implantation.

If marking of the aorta is also desired, the marking is done following completion of the size selection. The sizer/marker with the selected size is inserted into position within the patient's aorta. The orientation of the sizer/marker is properly adjusted prior to the marking. Once the appropriate position and orientation of the sizer/marker is obtained, the marking is performed. The marking can be done by pressing a knob, button, switch or other actuator on the handle of the sizer/marker to initiate the marking, as described above with respect to particular embodiments, and/or using a separate marker that is placed at particular position indicators on the prosthesis template of the sizer/marker. Marks are placed at appropriate locations relative to the prosthesis template to assist with implantation of the prosthesis.

The prosthesis with the selected size is then implanted. If markings have been made, these can be used to orient the prosthesis. Alternatively, the prosthesis can be oriented by eye. In some embodiments, the position of the markings specifically guides the placement of sutures or other fasteners, such as staples.

In the preferred embodiment, the sizer/marker posts and scallops are oriented to assure clearance of the coronary ostia. For example, marking at the inflow edge can result in three 120 degree spaced dye marks aligned in a plane slightly below the patient's excised aortic leaflets. Three sutures may then be placed using a vertical interrupted technique such that the distal end of each suture exits from the tissue at each mark. The distal suture ends are then passed through the inflow edge of the valve prosthesis at their corresponding 120 degree spaced markings. The sequence of suture routing, number of sutures, and method of suture placement may be at the discretion of the surgeon.

Simple interrupted suture are then placed in equal numbers between the three 120 degree sutures. A total of approximately 16 to 18 equally spaced, simple vertical interrupted sutures define the location of the inflow edge of the valve.

The sizer/marker 120 degree inflow marks locate the depth of the inflow suture plane. This assures that the prosthetic valve is implanted deep enough to clear the coronary ostia. The radial orientation of the three marks leads to the proper radial orientation of the prosthetic valve's commissure supports. During suturing of the prosthetic valve's outflow edge, the dye marks that were placed at the top of the sizer/marker posts guide the radial orientation of the valve commissure supports.

In preferred embodiments, the sizer/markers are reusable. Following use of the sizer/markers, all of the sizer/markers used in the procedure are sterilized prior to their next use. Appropriate sterilization procedures may depend on the materials used to form the sizer marker. Suitable sterilization procedures include, for example, chemical sterilization, radiation sterilization, and heat sterilization. Chemical sterilization can use aldehydes, peroxides or other chemical sterilants. Radiation sterilization can be based, for example, on an electron beam, ultraviolet light, gamma rays or other electromagnetic radiation. Heat sterilization, for example, can be performed in an autoclave, heated water or the like.

Distribution and Packaging

The sizer/markers generally are distributed as a set with at least one member of the set corresponding in size with the size of available prostheses. Thus, a sizer/marker will be available to evaluate the size of the annulus of the patient in relation to each available prosthesis. For convenience, all of the sizer/markers of a set can be placed within a single container, such as a box with slots for holding the sizer/markers. The container can be made to be compatible with radiation or heat sterilization, such that the sizer/markers can be sterilized within the container.

Generally, the sizer/markers are distributed to hospitals and any other location where valve replacement procedures are performed. Generally, the sizer/marker sets are distributed, such that they are available at the medical facility when needed. The sizer/markers can be distributed along with instructions for proper use along with any other desired or required documentation. The sizer/markers can be sterilized in storage, such that they are immediately ready for use, or they can be sterilized immediately prior to each use.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A tissue marking device comprising:
   a) a prosthesis template having a diameter approximately equal to the diameter of an aortic heart valve prosthesis, the prosthesis template comprising a marking element configured to mark tissue at fixed positions relative to the prosthesis template.

2. The tissue marking device of claim 1 wherein the prosthesis template has three posts along the top edge of the prosthesis template.

3. The tissue marking device of claim 2 wherein the three posts are located at positions approximately corresponding to the positions of the commissure supports of a porcine aortic heart valve.

4. The tissue marking device of claim 2 wherein the three posts are located symmetrically around the prosthesis template.

5. The tissue marking device of claim 2 wherein the three posts are located asymmetrically around the prosthesis template.

6. The tissue marking device of claim 2 wherein the three posts have equal height.

7. The tissue marking device of claim 2 wherein the three posts have different heights.

8. The tissue marking device of claim 1 wherein the prosthesis template comprises a transducer.

9. The tissue marking device of claim 1 further comprising a handle attached to the prosthesis template.

10. The tissue marking device of claim 9 wherein the handle comprises a grip and an extension, wherein the extension is connected to the grip and to the prosthesis template.

11. The tissue marking device of claim 9 wherein the handle extends in a direction corresponding generally to the outflow edge of the corresponding prosthesis.

12. The tissue marking device of claim 9 wherein the marking element comprises pores on the outer surface of the prosthesis template and wherein the handle comprises a reservoir of marking fluid and a plunger forming a surface of the reservoir, the handle and prosthesis template comprising channels connecting the reservoir and the pores.

13. The tissue marking device of claim 1 wherein the marking element comprises a channel connected to a vessel of cooling fluid, wherein the expansion of the cooling fluid is controlled by a valve.

14. The tissue marking device of claim 1 wherein the marking element comprises a resistive heater.

15. The tissue marking device of claim 1 wherein the marking element comprises an electromagnetic transmitter.

16. The tissue marking device of claim 1 wherein the marking element comprises electrical conductors placed to cauterize the tissue to provide the marks.

17. The tissue marking device of claim 1 wherein the marking element comprises a marking fluid delivering needle.

18. The tissue marking device of claim 1 wherein the prosthesis template comprises holes in its surface connected to a suction device.

19. A tissue marking device comprising:
a) a prosthesis template having a diameter approximately equal to the diameter of an aortic heart valve prosthesis; and
b) a marker having a marking tip that interfaces with the prosthesis template, wherein the marker is separately positionable from the prosthesis template.

20. The tissue marking device of claim 19 wherein the prosthesis template comprises a position indicator.

21. The tissue marking device of claim 19 further comprising a suture needle wherein application of the suture with the needle is guided by the prosthesis template.

22. The tissue marking device of claim 19 further comprising a handle attached to the prosthesis template.

23. The tissue marking device of claim 22 wherein the handle extends in a direction corresponding generally to the outflow edge of the corresponding prosthesis.

24. The tissue marking device of claim 19 wherein the prosthesis template has three posts along the top edge of the prosthesis template.

25. The tissue marking device of claim 24 wherein the three posts are located at positions approximately corresponding to the positions of the commissure supports of a porcine aortic heart valve.

26. The tissue marking device of claim 24 wherein the three posts are located symmetrically around the prosthesis template.

27. The tissue marking device of claim 24 wherein the three posts are located asymmetrically around the prosthesis template.

28. The tissue marking device of claim 19 wherein the marker comprises a marking fluid.

29. A tool comprising a prosthesis template, the prosthesis template comprising a generally annular base and a plurality of posts along the top edge extending upwardly from the annular base around the circumference of the annular base, the prosthesis template having an outer surface approximating the outer surface of a heart valve prosthesis.

30. The tool of claim 29 wherein the plurality of posts are three posts.

31. The tool of claim 30 wherein the three posts are located at positions approximately corresponding to the positions of the commissure supports of a porcine aortic heart valve.

32. The tool of claim 30 wherein the tree posts are located symmetrically around the prosthesis template.

33. The tool of claim 30 wherein the three posts are located asymmetrically around the prosthesis template.

34. The tool of claim 30 wherein the three posts have equal height.

35. The tool of claim 30 wherein the three posts have different height.

36. The tool of claim 29 wherein the prosthesis template has a diameter from about 13 mm to about 39 mm.

37. The tool of claim 29 further comprising a handle attached to the prosthesis template.

38. The tool of claim 37 wherein the handle extends generally in the direction of the posts.

39. The tool of claim 37 comprising a second prosthesis template extending from the handle in the opposite direction as the first prosthesis template.

40. A tool system comprising a plurality of tool elements of claim 29 wherein the plurality of tool elements include prosthesis templates with different diameters.

* * * * *